United States Patent [19]

Marquis et al.

[11] Patent Number: 4,654,427

[45] Date of Patent: Mar. 31, 1987

[54] SYNTHESIS OF MOLYBDENUM OXIDE/ALKANOL COMPLEXES

[75] Inventors: Edward T. Marquis, Austin; John R. Sanderson, Leander; Kenneth P. Keating, Georgetown; William A. Smith, Austin, all of Tex.

[73] Assignee: Texaco Inc., White Plains, N.Y.

[21] Appl. No.: 804,132

[22] Filed: Dec. 6, 1985

Related U.S. Application Data

[63] Continuation-in-part of Ser. No. 687,710, Dec. 31, 1984, abandoned.

[51] Int. Cl.[4] .............................................. C07F 11/00
[52] U.S. Cl. ..................................... 556/57; 502/171; 549/529
[58] Field of Search .......................................... 556/57

[56] References Cited

U.S. PATENT DOCUMENTS

| | | | |
|---|---|---|---|
| 2,795,552 | 6/1957 | Abbott et al. | 556/57 X |
| 3,121,059 | 2/1964 | DeYoung et al. | 556/61 X |
| 3,285,942 | 11/1966 | Price et al. | 556/57 |
| 3,480,563 | 11/1969 | Bonetti et al. | 556/57 X |
| 3,668,227 | 6/1972 | Mattucci et al. | 556/57 |
| 3,931,044 | 1/1976 | Maurin | 549/529 X |
| 3,956,180 | 5/1976 | Cavitt | 549/533 |
| 3,991,090 | 11/1976 | Hagstrom et al. | 556/57 |
| 4,009,122 | 2/1977 | Lines et al. | 556/57 X |
| 4,192,757 | 3/1980 | Brewster | 556/57 X |

*Primary Examiner*—Helen M. S. Sneed
*Attorney, Agent, or Firm*—Jack H. Park; Kenneth R. Priem

[57] ABSTRACT

Storage stable solutions of molybdenum/alkanol complexes in the alkanol are prepared by reacting a molybdenum oxide and ammonium hydroxide and an amount of a straight chain or branched chain $C_6$-$C_{13}$ alkanol, within the range of about 10 to about 55 moles of alkanol per gram atom of molybdenum sufficient to form a storage stable molybdenum/alkanol complex. The complex-forming reaction is initiated in the presence of about 1 to about 4 moles of water per gram atom of molybdenum and about 0.5 to about 10 moles of ammonia per gram atom of molybdenum, the water and ammonia preferably being added in the form of concentrated ammonium hydroxide. The reaction is conducted at a temperature of about 120° to about 190° C. for a period of time, normally about 3 to about 8 hours, sufficient to substantially completely remove ammonia and water to provide a liquid reaction product comprising said solution of molybdenum/alkanol complex dissolved in unreacted alkanol and containing about 0.001 to about 0.1 wt. % of water. The reaction product is filtered to provide a clarified storage stable solution of the molybdenum/alkanol complex having a dissolved molybdenum content of about 3 to about 10.5 wt. %.

12 Claims, No Drawings

SYNTHESIS OF MOLYBDENUM OXIDE/ALKANOL COMPLEXES

CROSS-REFERENCE TO RELATED APPLICATION

This application is a continuation-in-part of copending application Ser. No. 06/687,710 filed Dec. 31, 1984 and entitled "Improved Synthesis of Molybdenum/Alcohol Complexes Useful as Epoxidation Catalysts", now abandoned.

BACKGROUND OF THE INVENTION

1. Field of the Invention

The invention relates to the methods for making molybdenum complexes and more particularly relates to methods for making a molybdenum oxide/alkanol complex useful as an olefin epoxidation catalyst.

2. Other Related Methods in the Field

The epoxidation of olefins to give various epoxide compounds has long been an area of study by those skilled in the art. It is well known that the reactivities of the various olefins differ with the number of substituents on the carbon atoms involved in the double bond. Ethylene itself has the lowest relative rate of epoxidation, with propylene and other alpha olefins being the next slowest. Compounds of the formula $R_2C=CR_2$, where R simply represents alkyl or other substituents, may be epoxidized fastest. Thus, the more substituents on the double bond carbons, the easier it is to epoxidize across that bond.

The production of ethylene oxide from ethylene has long been known to be accomplished by reaction with molecular oxygen over a silver catalyst. Numerous patents have issued on various silver-catalyzed processes for the production of ethylene oxide. Unfortunately, the silver catalyst route will not work for olefins other than ethylene. For a long time the commercial production of propylene oxide could only be accomplished via the cumbersome chlorohydrin process.

A commercial process for the manufacture of substituted epoxides from alpha olefins such as propylene was not discovered until John Kollar's work in the 1960s. His U.S. Pat. No. 3,351,635 taught that an organic epoxide compound could be made by reacting an alpha olefin with and organic hydroperoxide in the presence of a molybdenum, tungsten, titanium, columbium, tantalum, rhenium, selenium, chromium, zirconium, tellurium or uranium catalyst. Kollar's, U.S. Pat. No. 3,350,422 teaches a similar process using a soluble vanadium catalyst.

However, even though Kollar's work has been recognized as extremely important in the development of a commercial propylene oxide process that did not depend on the chlorohydrin route, it has been recognized that Kollar's catalytic route (in which molybdenum is the preferred catalyst) has a number of problems. For example, if t-butyl hydroperoxide is used as the peroxide, large quantities of t-butyl alcohol corresponding to the peroxide are formed and the t-butyl alcohol that is recovered must be of marketable quantity. An especially troublesome class of by-products are the propylene oligomers. If propylene is used, various propylene dimers, sometimes called hexenes, are separated from the propylene oxide only with great difficulty. In addition, the molybdenum catalyst may not be stable or the recovery of the catalyst for recycle may be poor.

Various avenues of investigation have been explored in attempts to improve on the molybdenum-catalyzed epoxidation of propylene. One technique was to try to improve on the catalyst itself. Patents which cover the preparation of various molybdenum epoxidation catalysts include U.S. Pat. No. 3,362,972 to Kollar. There a hydrocarbon soluble salt of molybdenum or vanadium may be made by heating a molybdenum compound in which molybdenum has a valence of +6, or a vanadium compound in which vanadium has a valence of +5, with a carboxylic acid of from 4 to 50 carbon atoms having at least 4 carbon atoms per carboxylic group. U.S. Pat. No. 3,578,690 to Becker discloses that molybdenum acid salts may be made by directly reacting a carboxylic acid with a molybdenum compound while removing the water that is formed.

The reaction of molybdenum trioxide with monohydric saturated alcohols having 4 to 22 carbon atoms or with a mono- or polyalkylene glycol monoalkyl ether or mixtures thereof to make olefin epoxidation catalysts is described in U.S. Pat. No. 3,480,563 to Bonetti, et al. These catalysts have only 0.07 to 0.93% molybdenum, which is a molybdenum content too low for maximum economy in commercial use.

In U.S. Pat. No. 4,434,975 to ARCO, investigators found that molybdenum catalysts could be made from saturated alcohols or glycols having one to four carbon atoms, such as ethylene glycol and propylene glycol, by reacting them with molybdenum metal and an organic hydroperoxide, peroxide, or $H_2O_2$. Molybdenum compounds prepared by reacting an ammonium-containing molybdate with a hydroxy compound, for example, an organic primary or secondary alcohol, a glycol or a phenol, are described in U.S. Pat. Nos. 3,784,482 and 3,787,329 to Cavitt.

U.S. Pat. No. 3,573,226 to Sorgenti discloses that molybdenum-containing epoxidation catalyst solutions may be made by heating molybdenum powder with a stream containing unreacted tertiary butyl hydroperoxide and polyhydric compounds of from about 200 to 300 molecular weight and having from 4 to 6 hydroxyl groups per molecule.

U.S. Pat. No. 3,953,362 to Lines, et al. reveals that novel molybdenum epoxidation catalysts may be prepared by reacting an oxygen-containing molybdenum compound with hydrogen peroxide and an amine and optionally water or an alkylene glycol at elevated temperatures. Similar cataysts are prepared by reacting an oxygen-containing molybdenum compound with an amine and an alkylene glycol at elevated temperatures according to Lines, et al. U.S. Pat. No. 4,009,122.

SUMMARY OF THE INVENTION

This invention is directed to the preparation of storage stable solutions of molybdenum/alkanol complexes in the alkanol which are prepared by reacting a molybdenum oxide and an ammonia-liberating compound, preferably ammonium hydroxide with an amount of a straight chain or branched chain $C_6$–$C_{13}$ alkanol, within the range of about 10 to about 55 moles of alkanol per gram atom of molybdenum sufficient to form a storage stable molybdenum/alkanol complex. The complex-forming reaction is initiated in the presence of about 1 to about 4 moles of water per gram atom of molybdenum and about 0.5 to about 10 moles of ammonium ions per gram atom of molybdenum at a temperature of about 120° to about 190° C. to initiate the molybdenum/alkanol complex formation reaction and the reaction is continued for a period of time, normally about 3 to about 8 hours, sufficient to substantially completely remove ammonia and water to provide a liquid reaction product comprising said solution of molybdenum/alkanol complex dissolved in unreacted alkanol and containing about 0.001 to about 0.1 wt. % of water. The reaction product is filtered to provide a clarified storage stable solution of the molybdenum/alkanol complex having a dissolved molybdenum content of about 3 to about 10.5 wt. %. Normally, the amount of water present when the reaction is initiated is supplied by the water present in a concentrated solution of ammonium hydroxide. A concentrated solution of ammonium hydroxide will contain about 30-31 wt. % of ammonia, the balance being water.

DETAILED DESCRIPTION OF THE PREFERRED EMBODIMENT

The improvements in the complexes of this invention relate to the discovery that the initial molar ratio of alcohol, water and ammonium hydroxide to molybdenum compound and the reaction temperature effect the amount of soluble molybdenum that will be incorporated into the solubilized catalyst complex, the ease of filterability of the finished reaction mixture and the stability of the finished complex solution with respect to staying clear and solids-free over the useful life of the catalyst.

The molybdenum compounds used to make the complexes of this invention are oxygen-containing molybdenum compounds. Such materials include molybdenum trioxide and molybdenum sesquioxide.

The alcohols to be employed in the reaction to make the inventive complexes are primary straight chain or branched chain alkanols containing 6 to 13 carbon atoms such as hexyl alcohol, octyl alcohol, decyl alcohol, tridecyl alcohol, isohexyl alcohol, isooctyl alcohol, etc. As is hereinafter explained in greater detail, the preferred alkanol is 2-ethyl-1-hexyl alcohol.

Further (see Table I), it has been found that the ratio of alcohol to gram atoms of molybdenum, the ratio of concentrated ammonium hydroxide to gram atoms of molybdenum and the reaction temperature are important in determining the amount of molybdenum that is solubilized in the catalyst complex, the ease of processing of the complex during manufacture and also the storage stability of the finished complex.

Table II shows a comparison of several other alcohols along with 2-ethyl-1-hexanol in complex preparations which involve the reaction of $MoO_3$, concentrated ammonium hydroxide (30.5 wt. % ammonia) and the alcohol. In Examples 48 and 49 (utilizing 1-tetra decanol and 1-decanol) the percent molybdenum in the complex is substantially less than that with 2-ethyl-1-hexanol (Examples 8 and 9) and the percent molybdenum incorporated in the complex is also less. In Examples 51 and 52 (cyclohexanol and n-pentyl alcohol) the complexes filtered so slowly (took several days) as to make their preparation commercially not feasible. In Examples 53-56 (t-amyl, n-butyl, sec-butyl and tert-butyl alcohols) essentially no molybdenum was incorporated in these complexes. Thus, Table II shows that 2-ethyl-1-hexanol processes with ease while the other commercially available alcohols that were tested, such as hexyl, isooctyl, decyl and tridecyl alcohol were less easily processed.

2-Ethyl-1-hexanol is especially preferred because of its thermal stability and stability toward oxidation during the heating involved in preparing the catalyst (e.g., 3-8 hours at 175°-185° C.). Further 2-ethyl-1-hexanol imparts good filterability and storage stability to the complex. The use of ammonium hydroxide sharply increases (frequently doubles or triples) the amount of molybdenum that is solubilized in the complex preparation involving molybdenum trioxide and 2-ethyl-1-hexanol relative to the reaction of molybdenum trioxide and 2-ethyl-1-hexanol alone. In Example 1 (with $NH_4OH$) the molybdenum content was 2.07% and in Example 2 (identical to Example 1 except no $NH_4OH$) the molybdenum content was only 1.39%. Use of small amounts of concentrated ammonium hydroxide provide a definite improvement over the case where no ammonium hydroxide is employed. Large amounts of ammonium hydroxide provide no benefit beyond a certain optimum level. The optimum level of ammonium hydroxide to be used in reaction of molybdenum trioxide with 2-ethyl-1-hexanol can be determined by routine experiments. The optimal amount of ammonium hydroxide produces a maximum molybdenum concentration in the soluble complex while yet producing an easily filterable complex which remains stable and solids-free upon standing.

Water and ammonia should be removed during the course of the reaction. The use of azeotroping agents with the alcohol/ molybdenum trioxide/ammonium hydroxide reactant system speeds the complex preparation by driving off water and ammonia. However, use of an azeotroping agent can lead to a certain random instability upon standing. Complexes made with this technique may be clear and solids free for days or weeks and then form solids seemingly all at once.

For the 2-ethyl-1-hexanol, molybdenum trioxide/ammonium hydroxide system, the preferred reactant ratios are 10:1 to 55:1 expressed in terms of initial moles of alcohol to gram atoms of molybdenum in the molybdenum trioxide. An especially preferred range of moles of alcohol to gram atoms of molybdenum is 10:1 to 20:1. At least one-half mole of ammonium hydroxide per gram atom of molybdenum should be used, with about 10:1 moles of $NH_4OH$ to gram atom molybdenum being the upper limit. To provide the best complex in terms of molybdenum content, ease of processing and stability upon standing the ratio of moles of ammonium hydroxide to gram atoms of molybdenum should preferably be 1:1 to 5:1. The reaction temperature to make the inventive complexes should be between 120° and 190° C., preferably between 150° and 185° C., and the pressure should be atmospheric. Reaction temperatures of 175°-185° C. drive off the water and ammonia present in the reaction mixture. With the technique of this invention, molybdenum contents of 3 to 6.5% are possible. Separation is done by filtration. The complexes and method of this invention involving 2-ethyl-1-hexanol, reacted with molybdenum trioxide in the presence of concentrated ammonium hydroxide, are more particularly illustrated by the following Examples which should not be construed as limiting the invention in any way. The examples also illustrate the use of the complexes of this invention as catalysts in an epoxidation reaction.

EXAMPLE 1

(5780-30)

To a 500 ml or one liter Morton flask equipped with mechanical stirrer, Dean Stark trap, condenser, thermometer, and nitrogen inlet and bubbler were added 7.75 g MoO₃ (Climax Grade M) and 260.46 g of 2-ethyl-1-hexanol (2.0 moles or 37.14:1 ratio of moles alcohol/-gram atom of molybdenum) followed by 5 ml of concentrated ammonium hydroxide (30.6 wt. % ammonia). The contents were heated slowly with stirring to 180° to 183° C. This temperature was held for three to four hours. The reactor contents were cooled and filtered to yield a filtrate of 254.1 g. Reaction details and product characteristics are given in Table I.

EXAMPLE 2

(5780-27)

Comparative Example Without NH₄OH

This example was run exactly like Example 1 except that no ammonium hydroxide was added. Only 1.39% of the catalyst was molybdenum as opposed to 2.07% for the catalyst of Example 1. Reaction details and product characteristics are given in Table I.

EXAMPLE 3

(5780-33)

To a 500 ml or one liter Morton flask equipped with mechanical stirrer, Dean Stark trap, condenser, thermometer, and nitrogen inlet and bubbler were added 7.75 g MoO₃ (Climax Grade M) (0.0538 moles) and 260.46 g of 2-ethyl-1-hexanol (2.0 moles or a 37.14:1 ratio of moles ROH/g atoms molybdenum) followed by 20 ml of concentrated NH₄OH (30.6 wt. % ammonia). The contents were heated with stirring to 180° to 183° C. and held there for three to four hours. The product was cooled and filtered to leave a filtrate of 249.0 g. Reaction and product details are given in Table I.

EXAMPLE 4

(5780-58)

To a one liter Morton flask equipped with mechanical stirrer, Dean Stark trap, condenser, thermometer, nitrogen inlet and bubbler was added 29.0 g MoO₃ (Climax Grade M) followed by 299.5 g of 2-ethyl-1-hexanol (Alfa). The mole ratio of alcohol to grams of molybdenum was 11.43:1. Twenty ml of concentrated ammonium hydroxide (30.6 wt. % ammonia) were added to the flask. The contents were slowly heated to 180° C. and the time and temperature were recorded about every hour. At that time water was removed. If an azeotropic agent such as toluene were to be used, it would also be taken off. After the reaction was over (generally taken as at least five hours at 180° C.), the contents were cooled to about 50° C. and filtered. The product filtered very slowly through glass filter paper at room temperature. The weight of the filtrate was 290.5 g. Reaction and product details are given in Table I.

This complex was used in the propylene epoxidation of Example 5.

EXAMPLE 5

Propylene Epoxidation

To a nitrogen purged 300 ml 316 stainless steel autoclave were added at room temperature 43.0 g (1.0238 moles) propylene followed by 88.5 g of a premixed solution of TBHP and molybdenum complex to serve as catalyst. The TBHP part of the premixed TBHP/catalyst solution consisted of 87.7 g of solution containing 60.50% TBHP, 39.30% TBA, and 0.2% water. The molybdenum catalyst part of the premixed solution consisted of 0.8 g of molybdenum 2-ethyl-1-hexanol complex (6.50% molybdenum) made in Example 4.

The autoclave containing the propylene (43.0 g, 1.0238 moles) and the premixed TBHP/molybdenum catalyst solution (53.0585 g TBHP, 0.5895 moles TBHP) was heated to 110° C. over a 30 minute period and held there at 110° C. for 90 minutes. The propylene to TBHP mole ratio in this run was 1.74:1 and the TBHP/TBA mole ratio was 1.27:1 and the amount of catalyst utilized was 0.0395 wt. % basis total reactor charge. The reaction mixture was cooled and analyzed.

Total product weighed 131.5 grams
Total liquid product = 100.8 grams
TBHP found remaining in liquid product, %  1.10
TBHP remaining, g  1.1088
moles TBHP remaining  0.0123
moles TBHP reacted = moles TBHP fed − moles TBHP remaining
moles TBHP reacted = 0.5895 − 0.0123 = 0.5772

$$\text{Conversion} = \frac{\text{moles TBHP reacted}}{\text{moles TBHP fed}} = \frac{0.5772}{0.5895} = 97.91\%$$

The total product was analyzed and found to contain 25.147 wt. % propylene oxide and 13.889% propylene.

grams propylene oxide = 33.0683
moles propylene oxide = 0.5701
Selectivity to PO =

$$\frac{\text{moles PO}}{\text{moles TBHP consumed (reacted)}} = \frac{0.5701}{0.5772} = 98.78\%$$

Propylene oxide yield =

$$\frac{\text{moles PO formed}}{\text{moles TBHP fed}} = \frac{0.5701}{0.5895} = 96.71\%$$

EXAMPLE 6

(5810-14)

To a one liter Morton flask equipped with mechanical stirrer, Dean Stark trap, thermometer nitrogen inlet and bubbler were added 17.84 g MoO3 (Climax Grade M) followed by 299.5 g of 2-ethyl-1-hexanol (Alfa). The mole ratio alcohol to grams of molybdenum was 18.57:1. Ten ml of concentrated ammonium hydroxide were also added to the flask.

The reaction mixture was heated slowly to 180° C. Times were recorded and water was removed as in Example 4. The weight of the filtrate was 285.0 g. Reaction and product details are given in Table I.

EXAMPLE 7

(5810-15)

To a one liter Morton flask equipped with mechanical stirrer, Dean Stark trap, condenser, thermometer, nitrogen inlet and bubbler were added 17.84 g MoO3 (Climax Grade M) followed by 299.5 g of 2-ethyl-1-hexanol (Alfa). Mole ratio alcohol to grams of molybdenum was 18.57:1. Finally, 12.5 ml of concentrated ammonium hydroxide (30.6 wt. % ammonia) was added.

Again, the reactor contents were slowly heated to 180° C. Time, temperature and amount of water removal were recorded. After at least 5.0 hours at 180° C., the product was cooled to about 50° C. and filtered. The total weight of the filtrate was 282.2 g. Reaction and product details are given in Table I.

EXAMPLE 8

(5810-16)

To a one liter Morton flask equipped with mechanical stirrer, Dean Stark trap, condenser, thermometer, nitrogen inlet and bubbler were added 17.84 g MoO3 (Climax Grade M) followed by 299.5 g of 2-ethyl-1-hexanol (Alfa). Mole ratio alcohol to grams of molybdenum was 18.57:1. Fifteen ml of concentrated ammonium hydroxide (30.6 wt. % ammonia) were added last. Heating and product recovery were conducted as in Example 7. Weight of the filtrate was 290.0 g. See Table I for details.

EXAMPLE 9

(5810-17)

To a one liter Morton flask equipped with mechanical stirrer, Dean Stark trap, condenser, thermometer, nitrogen inlet and bubbler were added 17.84 g MoO3 (Climax Grade M) followed by 299.5 g of 2-ethyl-1-hexanol (Alfa). Mole ratio alcohol to grams of molybdenum was 18.57:1. Subsequently, 17.5 ml concentrated ammonium hydroxide (30.6 wt. % ammonia) were added. Heating and product recovery were conducted as in Example 7. Weight of the filtrate was 298.8 g. See Table I for details.

Following the procedure of Example 7, twenty-four additional complexes were prepared, as summarized in Table I. In Table I note that, for comparative purposes, some of the runs are reported in duplicate.

TABLE I

Catalysts Made by Reacting Molybdenum Trioxide and 2-Ethyl-1-Hexanol in the Presence of Varying Amounts of Conc $NH_4OH$

| NB Run # | Grams of 2-Ethyl Hexanol | Grams of $MoO_3$ | Mole Ratio Alcohol/ G. A. Moly | G. A. Moly (Gram Atoms of Moly) | Mole Ratio $NH_3$/ G. A. Moly | Mole Ratio $H_2O$/ G. A. Moly | Wt. % Moly in the Catalyst |
|---|---|---|---|---|---|---|---|
| 5780-35 | 299.5 | 29.00 | 11.43/1 | 0.2014 | 0.00 | 0.00 | 1.01 |
| 5780-42 | " | " | " | " | 0.00 | 2.76 | 0.67 |
| 5780-44 | " | " | " | " | 0.00 | 5.52 | 0.08 |
| 5780-53 | " | " | " | " | 0.00 | 0.00 | 2.49 |
| 5780-60 | " | " | " | " | 0.00 | 2.76 | 2.22 |
| 5780-62 | " | " | " | " | 0.00 | 5.52 | 2.00 |
| 5780-38 | " | " | " | " | 0.80 | 1.71 | 0.22 |
| 5780-56 | " | " | " | " | 0.80 | 1.71 | 4.00 |
| 5780-40 | " | " | " | " | 1.60 | 3.42 | 3.37 |
| 5780-58 | " | " | " | " | 1.60 | 3.42 | 6.50 |
| 5780-53 | " | " | " | " | 0.00 | 0.00 | 2.49 |
| 5810-7 | " | " | " | " | 0.16 | 0.34 | 2.60 |
| 5780-64 | " | " | " | " | 0.24 | 0.86 | 2.72 |
| 5780-56 | " | " | " | " | 0.80 | 1.71 | 4.00 |
| 5810-8 | " | " | " | " | 1.20 | 2.57 | 5.85 |
| 5810-9 | " | " | " | " | 1.40 | 2.99 | 6.05 |
| 5780-58 | " | " | " | " | 1.60 | 3.42 | 6.50 |
| 5780-71 | 299.50 | 20.73 | 16.00/1 | 0.1440 | 1.12 | 2.39 | 4.18 |
| 5780-72 | " | " | " | " | 1.40 | 2.99 | 4.33 |
| 5780-74 | " | " | " | " | 1.96 | 4.19 | 4.63 |
| 5780-78 | " | " | " | " | 3.08 | 6.58 | 4.84 |
| 5780-26 | 260.46 | 15.51 | 18.57/1 | 0.1077 | 0.00 | 0.00 | 0.54 |
| 5810-14 | 299.50 | 17.84 | " | 0.1239 | 1.30 | 2.78 | 3.80 |
| 5810-15 | " | " | " | " | 1.62 | 3.48 | 3.90 |
| 5810-16 | " | " | " | " | 1.94 | 4.17 | 3.90 |
| 5810-17 | " | " | " | " | 2.28 | 4.87 | 3.90 |
| 5810-21 | " | " | " | " | 3.58 | 7.65 | 4.00 |
| 5810-22 | " | 15.00 | 22.10/1 | 0.1042 | 0.77 | 1.65 | 2.63 |
| 5810-24 | " | " | " | " | 1.54 | 3.31 | 2.97 |
| 5810-25 | " | " | " | " | 1.93 | 4.13 | 3.39 |
| 5810-28 | " | " | " | " | 3.09 | 6.62 | 3.30 |
| 5780-27 | 260.46 | 7.75 | 37.17/1 | 0.0538 | 0.00 | 0.00 | 1.39 |
| 5780-30 | " | " | " | " | 1.49 | 3.20 | 2.07 |
| 5780-33 | " | " | " | " | 5.98 | 12.81 | 2.11 |
| 5780-28 | " | 6.30 | 45.70/1 | 0.0438 | 0.00 | 0.00 | 1.22 |
| 5780-29 | " | 5.30 | 54.32/1 | 0.0368 | 0.00 | 0.00 | 1.12 |

| NB Run # | % Moly Incorp in the Sol Cat | Amt. S'ld | Ease of Filtration | Rxn. Temp C. | Rxn Time Hrs | Wt. % $N_2$ in Cat. | Ml of $H_2O$ Taken Ov'hd |
|---|---|---|---|---|---|---|---|
| 5780-35 | 14.96 | ND | ND | 150–152 | 5.0 | ND | 1.0 |
| 5780-42 | 9.95 | ND | ND | 151–153 | 5.0 | ND | 7.5 |
| 5780-44 | 1.17 | ND | ND | 151–153 | 5.0 | ND | 17.0 |
| 5780-53 | 34.78 | ND | ND | 177 | 5.0 | ND | 5.0 |
| 5780-60 | 31.50 | ND | ND | 180 | 5.0 | ND | 12.0 |
| 5780-62 | 29.24 | ND | ND | 180 | 5.0 | ND | 22.0 |
| 5780-38 | 4.29 | ND | ND | 150–153 | 5.5 | 0.03 | 3.0 |
| 5780-56 | 59.45 | ND | ND | 180–182–182 | 5.0 | 0.29 | 14.5 |
| 5780-40 | 50.56 | ND | ND | 150–153 | 5.0 | 0.09 | 12.0 |
| 5780-58 | 97.68 | Few | VSlow | 180 | 5.0 | 0.22 | 21.0 |
| 5780-53 | 34.78 | ND | ND | 177 | 5.0 | ND | 5.0 |
| 5810-7 | 36.32 | ND | ND | 170–181–181 | 5.0 | 0.06 | 4.5 |
| 5780-64 | 40.10 | ND | ND | 180–180–180 | 5.0 | 0.24 | 4.5 |

TABLE I-continued
Catalysts Made by Reacting Molybdenum Trioxide and 2-Ethyl-1-Hexanol in the Presence of Varying Amounts of Conc NH₄OH

| | | | | | | | |
|---|---|---|---|---|---|---|---|
| 5780-56 | 59.45 | ND | ND | 180-182-182 | 5.0 | 0.29 | 14.5 |
| 5810-8 | 84.74 | ND | ND | 170-179-178 | 5.0 | 0.26 | 23.0 |
| 5810-9 | 84.22 | ND | ND | 179-181-180 | 5.0 | 0.34 | 23.0 |
| 5780-58 | 97.68 | Few | VSlow | 180 | 5.0 | 0.22 | 21.0 |
| 5780-71 | 58.02 | Mod | Slow | 181-183-177 | 5.0 | 0.19 | 15.0 |
| 5780-72 | 91.51 | Mod | Slow | 178-179-170 | 5.0 | 0.19 | 19.0 |
| 5780-74 | 98.26 | Mod | Slow | 178-178-170 | 5.0 | 0.19 | 23.0 |
| 5780-78 | 99.49 | Mod | Slow | 181-182-173 | 5.0 | 0.18 | 30.0 |
| 5780-26 | 12.61 | ND | ND | 182-183 | 5.0 | 0.10 | 3.0 |
| 5810-14 | 91.08 | Few | Fast | 176-177-173 | 5.0 | 0.04 | 15.0 |
| 5810-15 | 92.56 | Few | Fast | 178-180-178 | 5.0 | 0.17 | 15.5 |
| 5810-16 | 95.12 | Few | Fast | 176-179-172 | 5.0 | 0.20 | 19.5 |
| 5810-17 | 98.01 | Few | Fast | 180-180-176 | 5.0 | 0.01 | 20.0 |
| 5810-21 | 97.56 | ND | ND | 180-180-180 | 5.0 | 0.12 | 26.5 |
| 5810-22 | 74.06 | ND | ND | 178-180-179 | 5.0 | 0.08 | 7.5 |
| 5810-24 | 86.31 | ND | ND | 176-180-173 | 5.0 | 0.17 | 14.5 |
| 5810-25 | 95.84 | ND | ND | 180-180-180 | 5.0 | 0.16 | 15.0 |
| 5810-28 | 96.10 | ND | ND | 177-177-172 | 5.0 | 0.14 | 22.0 |
| 5780-27 | 62.23 | Few | Fast | 182-183 | 5.0 | 0.01 | 2.0 |
| 5780-30 | 101.80 | Few | Fast | 177-183 | 3.5 | 0.06 | 6.5 |
| 5780-33 | 101.70 | Few | Fast | 180-182 | 4.0 | 0.07 | 17.0 |
| 5780-28 | 67.55 | ND | ND | 180-181 | 4.0 | 0.04 | 0.5 |
| 5780-29 | 75.65 | ND | ND | 180-182 | 5.0 | 0.08 | 1.0 |

Turning now to Tables I and I-A and to Runs 5780-35, 5780-42 and 5780-44 of Table I, note when the reaction was conducted in the absence of ammonia at a temperature of about 150°-153° C., the filtered reaction product contained about 0.1 to 1 wt. % of soluble molybdenum. When the temperature was raised to about 177°-180° C., the amount of molybdenum that was solubilized more than doubled to about 2 to 2.5 wt. %. When all of the runs conducted at 150°-153° C. are considered, it will be seen that the use of 0.8 mole of ammonia per gram atom of molybdenum (run 5780-38) gave a result (0.2 wt. % of solubilized molybdenum) analogous to the results obtained in runs 5780-35, 5780-42 and 5780-44 conducted in the absence of added ammonia, but that the use of 1.6 moles of ammonia per gram atom of molybdenum (runs 5780-40) significantly increased the amount of solubilized molybdenum to about 3.4 wt. %. When runs conducted at about 180° C. are compared, it is to be noted that the percentage of solubilized molybdenum increased from about 2 wt. % without added ammonia (runs 5780-60 and 5780-62) to about 4 wt. % when about 0.8 mole of ammonia per gram atom of molybdenum was added (runs 5780-56) and to about 6.5 wt. % when 1.6 moles of ammonia per gram atom of molybdenum was used (run 5780-58).

This phenomenon is again demonstrated in runs conducted at about 180° C. with the use of progressively increased amounts of ammonia in the set of data reported for runs 5780-53, 5810-7, 5780-64, 5780-56, 5810-8, 5810-9 and 5780-58. The invention is further illustrated by the additional data reported in Tables I and I-A. Note, for example, from Table I-A, runs 5780-28 and 5790-29 that even at very high ratios of alcohol to gram atoms of molybdenum, only about 1.1 to about 1.2 wt. % of molybdenum was solubilized in the absence of added ammonia and water in the form of concentrated ammonium hydroxide.

TABLE II
COMPLEX PREPARATION
Comparing Other Alcohols With 2-Ethyl-1-Hexanol Reacting With MoO₃ and NH₄OH

| Example (Complex Preparation) | Alcohol | Reaction Temp., °C. | Reaction Time, Hours | Mole Ratio Alcohol/ g atoms Molybdenum | Mole Ratio Ammonia/ g atoms Molybdenum | Molybdenum in Complex, wt. % | Molybdenum Incorporated, % | Ease of Processing of Complex |
|---|---|---|---|---|---|---|---|---|
| 48 | 1-tetradecanol | 180-83 | 5.0 | 18.57:1 | 2.0:1 | 1.62 | 66.48 | Difficult |
| 49 | 1-decanol | 182-83 | 5.0 | " | " | 2.82 | 83.10 | Average |
| 51 | cyclohexanol | 154-56 | 6.0 | " | " | 4.68 | Low, could not complete filtration | Impossible, very difficult |
| 52 | n-pentyl | 133-37 | 6.0 | " | " | 5.24 | Low, could not complete filtration | Impossible, very difficult |
| 53 | t-amyl | 90-93 | 6.5 | " | " | 0 | 0 | Easy, but no molybdenum |
| 54 | n-butyl | 104-112 | 6.5 | " | " | 0 | 0 | Easy, but no molybdenum |
| 55 | sec-butyl | 89-90 | 6.0 | " | " | 0 | 0 | Easy, but no molybdenum |
| 56 | tert-butyl | 80 | 6.0 | " | " | 0 | 0 | Easy, but no molybdenum |
| 8 | 2-ethyl-1-hexanol | 172-79 | 5.0 | " | 1.94:1 | 3.90 | 95.12 | Excellent |
| 9 | 2-ethyl-1-hexanol | 176-180 | 5.0 | " | 2.28:1 | 3.90 | 98.01 | Excellent |

Many modifications may be made by one skilled in the art in this invention without changing the spirit and scope thereof which are defined only in the appended claims. The complexes of this invention have a high molybdenum content, are stable upon standing and are easily filterable, and provide better epoxidation results in terms of selectivity to propylene oxide and low propylene dimer make and high propylene oxide concentrations than any catalysts mentioned the journal or patent literature, especially at the low propylene to TBHP ratios examined.

We claim:

1. A method of preparing a storage stable solution of a catalytically active complex of molybdenum with a primary straight chain or branched chain alkanol containing 6 to 13 carbon atoms in said alkanol which comprises:

reacting a molybdenum oxide with said alkanol in the presence of ammonium hydroxide, within the range of about 10 to about 55 mols of alkanol per gram atom of molybdenum, a sufficient to form a storage stable molybdenum/alkanol complex, said reaction being initiated in the presence, based on said ammonium hydroxide, of about 1 to about 4 mols of water per gram atom of molybdenum and about 0.5 to about 10 mols of ammonia per gram atom of molybdenum, said reaction being initiated and continued at a temperature of about 120° to about 190° C. and continuing said reaction for a period of time within the range of about 3 to about 8 hours sufficient to substantially completely remove ammonia and water and to provide a liquid reaction product having said molybdenum/alkanol complex dissolved in unreacted alkanol and about 0.001 to about 0.1 wt. % of water, and recovering a clarified, storage stable solution of said catalytically active molybdenum/alkanol complex in said alknaol, said solution having a dissolved molybdenum content of about 3 to about 10.5 wt. %.

2. A method as in claim 1 wherein the mol ratio of alkanol to gram atoms of molybdenum is within the range of about 8.5 to about 15 and the reaction temperature is within the range of about 150° to about 185° C.

3. A method as in claim 2 wherein the alkanol is a hexyl alcohol.

4. A method as in claim 2 wherein the alkanol is iosoctyl alcohol.

5. A method as in claim 2 wherein the alkanol is decyl alcohol.

6. A method as in claim 2 wherein the alkanol is tridecyl alcohol.

7. A method of preparing a storage stable solution of catalytically active complex of molybdenum trioxide with 2-ethyl hexanol in 2-ethyl hexanol which comprises:

reacting molybdenum trioxide with 2-ethyl hexanol in amount within the range of from about 10 to about 55 mols of said 2-ethyl hexanol per gram atom of molybdenum, in the presence of concentrated ammonium hydroxide; said reaction being initiated in the presence, based on said concentrated ammonium hydroxide, of about 1 to about 4 mols of water per gram atom of molybdenum and about 0.5 to about 10 mols of ammonia per gram atom of molybdenum; said reaction being initiated and continued at a temperature of about 120° to about 190° C. and continuing said reaction for a period of time within the range of about 3 to about 8 hours sufficient to substantially completely remove ammonia and water and to provide a liquid reaction product comprising said molybdenum/2-ethylhexanol complex dissolved in 2-ethyl hexanol and containing about 0.001 to about 0.1 wt. % of water, and recovering a clarified, storage stable solution of said catalytically active molybdenum/2-ethyl hexanol complex in 2-ethyl hexanol, said solution having dissolved molybdenum content of about 3 to about 10.5 wt. %.

8. A method as in claim 7 wherein the temperature is within the range of about 150° to about 185° C.

9. A method as in claim 7 wherein the temperature is within the range of about 175° to about 185° C.

10. A storage stable solution of a catalytically active complex of molybdenum with 2-ethyl hexanol in 2-ethyl hexanol containing about 3 to about 10 wt. % of dissolved molybdenum and about 0.001 to about 0.1 wt. % of water prepared by the process of claim 7.

11. A storage stable solution as in claim 10 wherein the solution of the molybdenum/2-ethyl hexanol complex in 2-ethyl hexanol has a dissolved molybdenum content of about 3 to about 6.5 wt. %.

12. A method as in claim 1 wherein the recovered clarified storage stable solution of the molybdenum/alkanol complex in the alkanol has a dissolved molybdenum content of about 3 to about 6.5 wt. %.

* * * * *